United States Patent
Desfougeres et al.

(10) Patent No.: US 9,090,917 B2
(45) Date of Patent: Jul. 28, 2015

(54) INDUSTRIAL YEAST CAPABLE OF PRODUCING ETHANOL FROM AT LEAST ONE PENTOSE

(75) Inventors: Thomas Desfougeres, Neuville en Ferrain (FR); Georges Pignede, Marcqen-Baroeul (FR); Christophe Rave, Lambersart (FR); Jean-Michel Bavouzet, Croix (FR); Didier Colavizza, Roubaix (FR)

(73) Assignee: LESAFFRE ET COMPAGNIE, Paris (FR)

( * ) Notice: Subject to any disclaimer, the term of this patent is extended or adjusted under 35 U.S.C. 154(b) by 0 days.

(21) Appl. No.: 13/641,068

(22) PCT Filed: Apr. 4, 2011

(86) PCT No.: PCT/FR2011/050750
§ 371 (c)(1),
(2), (4) Date: Oct. 12, 2012

(87) PCT Pub. No.: WO2011/128552
PCT Pub. Date: Oct. 20, 2011

(65) Prior Publication Data
US 2013/0040353 A1 Feb. 14, 2013

(30) Foreign Application Priority Data

Apr. 14, 2010 (FR) ..................................... 10 01583
Apr. 30, 2010 (FR) ..................................... 10 01853

(51) Int. Cl.
| | |
|---|---|
| *C12P 7/06* | (2006.01) |
| *C12N 1/00* | (2006.01) |
| *C12N 15/74* | (2006.01) |
| *C12P 7/10* | (2006.01) |
| *C12N 1/22* | (2006.01) |
| *C12N 15/01* | (2006.01) |
| *C12R 1/865* | (2006.01) |

(52) U.S. Cl.
CPC ... *C12P 7/10* (2013.01); *C12N 1/22* (2013.01); *C12N 15/01* (2013.01); *C12R 1/865* (2013.01); *Y02E 50/16* (2013.01); *Y02E 50/17* (2013.01)

(58) Field of Classification Search
CPC .......... C12N 1/22; C12N 15/01; Y02E 50/17; Y02E 50/16; C12R 1/865; C12P 7/10
USPC ............. 435/161, 254.11, 254.2, 254.21, 471
See application file for complete search history.

(56) References Cited

U.S. PATENT DOCUMENTS

| | | | |
|---|---|---|---|
| 8,367,393 B2 * | 2/2013 | Hahn-Hagerdal et al. ......... | 435/252.35 |
| 2009/0246844 A1 | 10/2009 | Khramtsov | |

FOREIGN PATENT DOCUMENTS

| | | |
|---|---|---|
| WO | WO 2004/046333 | 6/2004 |
| WO | WO 2009/109634 | 9/2009 |

OTHER PUBLICATIONS

Karhumaa et al., Proteome analysis of the xylose-fermenting mutant yeast strain TMB 3400. Yeast, 2009, vol. 26: 371-382.*
Ohgren et al., Simultaneous saccharification and co-fermentation of glucose and xylose in steam-pretreated corn stover at high fiber content with *Saccharomyces cerevisiae* TMB3400. J. Biotechnol., 2006, vol. 126: 488-498.*
Oskar Bengtsson, et al., Xylose Reductase From *Pichia stipites* With Altered Coenzyme Preference Improves Ethanolic Xylose Fermentation by Recombinant *Saccharomyces cerevisiae*, Biotechnology for Biofuels (2009) 2:9, p. 1-10.
Bärbel Hahn-Hägerdal, et al., Towards Industrial Pentose-Fermenting Yeast Strains, Appl. Microbiol. Biotechnol. (2007) vol. 74, p. 937-953.
Marie Jeppsson, et al., The Expression of a *Pichia stipites* Xylose Reductase Mutant With Higher $K_M$ for NADPH Increases Ethanol Production From Xylose in Recombinant *Saccharomyces cerevisiae*, Biotechnology and Bioengineering (2006) vol. 93, No. 4, p. 665-673.
Marko Kuyper, et al., Evolutionary Engineering of Mixed-Sugar Utilization by a Xylose-Fermenting *Saccharomyces cerevisiae* Strain, FEMS Yeast Research (2005) vol. 5, p. 935-934.
Marko Kuyper, et al., Minimal Metabolic Engineering of *Saccharomyces cerevisiae* for Efficient Anaerobic Xylose Fermentation: A Proof of Principle, FEMS Yeast Research (2004) vol. 4, p. 655-664.
Akinori Matsushika, et al., Expression of Protein Engineered $NADP^+$-Dependent Xylitol Dehydrogenase Increases Ethanol Production From Xylose in Recombinant *Saccharomyces Cerevisiae*, Appl. Microbiol. Biotechnol. (2008) vol. 81, p. 243-255.
Akinori Matsushika, et al., Bioethanol Production Performance of Five Recombinant Strains of Laboratory and Industrial Xylose-Fermenting *Saccharomyces cerevisiae*, Bioresource Technology (2009) vol. 100, p. 2392-2398.
Susumu Nagai, et al, A New Evidence for Induction of Respiration Deficiency in Yeast by Acriflavine, Experientia (1958) vol. XIV/9.
Marco Sonderegger, et al., Evolutionary Engineering of *Saccharomyces cerevisiae* for Anaerobic Growth on Xylose, Applied and Environmental Microbiology (2003) vol. 69, No. 4, p. 1990-1998.
Antonius J. van Mans, et al., Development of Efficient Xylose Fermentation in *Saccharomyces cerevisiae*: Xylose Isomerase as a Key Component, Adv. Biochem. Engin/Biotechnol (2007) vol. 108, p. 179-204.

(Continued)

*Primary Examiner* — Ganapathirama Raghu
(74) *Attorney, Agent, or Firm* — Vedder Price P.C.; Thomas J. Kowalski; Deborah L. Lu

(57) ABSTRACT

The present invention relates to the field of methods for obtaining ethanol-producing yeast strains, to the field of the thus produced strains and to the field of the industrial production of ethanol from said strains. Particularly, the present invention relates, in the most general aspect thereof, to a method for preparing yeasts from industrial *Saccharomyces cerevisiae* strains, to said strains, and to the use thereof in the industrial production of ethanol from industrial media containing at least one pentose.

11 Claims, 12 Drawing Sheets

(56) References Cited

OTHER PUBLICATIONS

Figure 1:
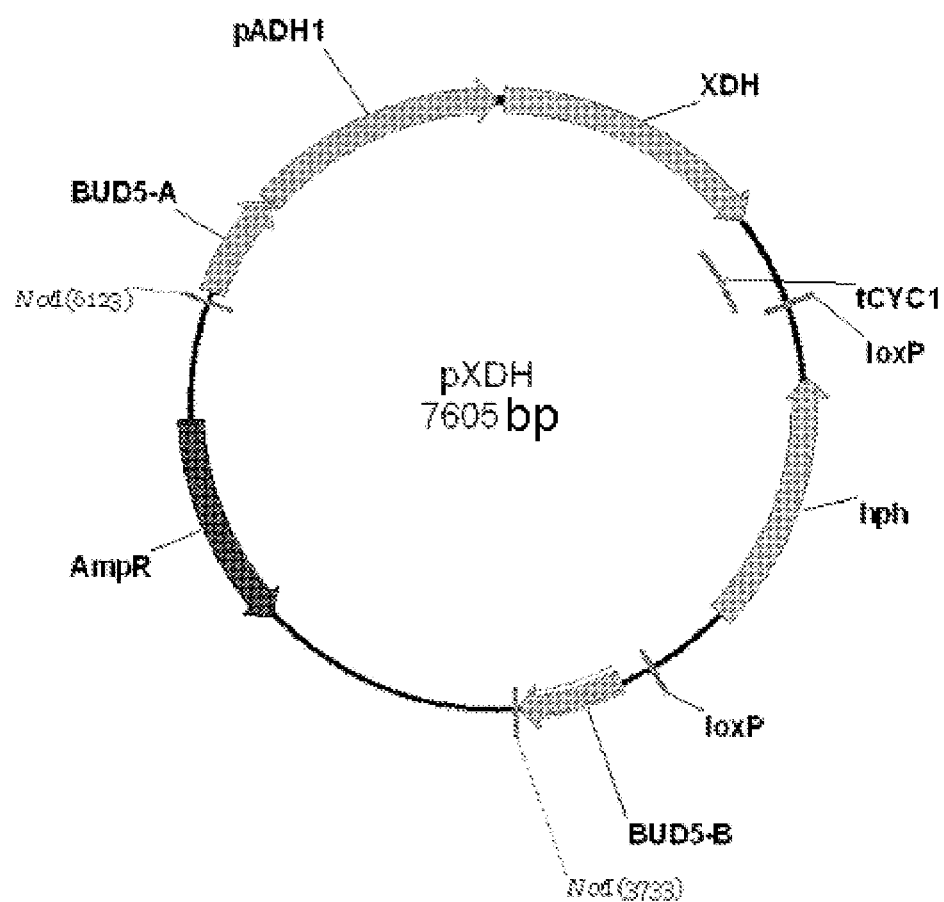

Seiya Watanabe, et al., Ethanol Production From Xylose by Recombinant *Saccharomyces cerevisiae* Expressing Protein-Engineered NADH-Preferring Xylose Reductase From *Pichia stipites*, Microbiology (2007) vol. 153, p. 3044-3054.

Karhumm, Kaisa, et al., "Co-utilization of L-arabinose and D-xylose by laboratory and industrial *Saccharomyces cervisiae* strains," Microbial Cell Facories2006, 5:18, Apr. 10, 2006, pp. 1-11.

Schacherer, Joseph et al., "Comprehensive polymorphism survey elucidates population structure of *S. cerevisiae*," Nature, Mar. 19, 2009, 458(7236) 342-345.

Van Dijken, J.P., et al., "An interlaboratory comparision of physiological and genetic properties of four *Saccharomyces cerevisiae* strains," Elsevier, Enzyme and Microbial Technology 26 (2000) pp. 706-714.

Traff-Bjerre, K.L., "Endogenous NADPH-dependent aldose reductase activity influences product formation during xylose consumption in recombinant *Saccaromyces cerevisiae*," Yeast, 2003 John Wiley & Sons, Ltd., 2004; 21: pp. 141-150.

Karhumaa, Kaisa, et al., "Investigation of limiting metabolic steps in the utilization of xylose by recombinant *Saccaromyces cerevisiae* using metabolic engineering," Yeast, 2005 John Wiley & Sons, Ltd., 22" [[/ 359-368.

Otero, Jose Manuel, et al., "Whole genome sequencin of *Saccaromyces cerevisiae*: from genotype to phenotype for improved metabolic engineering applications," BMC Genomics, 2010, 11:723.

\* cited by examiner

INDUSTRIAL YEAST CAPABLE OF PRODUCING ETHANOL FROM AT LEAST ONE PENTOSE

RELATED APPLICATIONS

The present application is filed pursuant to 35 U.S.C. §371 as a U.S. National Phase application of International Patent Application No. PCT/FR2011/050750, which was filed on Apr. 4, 2011, and published as WO 2011/128552 on Oct. 20, 2011, claiming the benefit of priority to French Patent Application No. FR 10 01583 filed on Apr. 14, 2010 and French Patent Application No. FR 10 01853 filed on Apr. 30, 2010. The entire content of each of the aforementioned applications is incorporated herein by reference in its entirety.

The present invention relates to the field of methods for obtaining ethanol-producing yeast strains, the yeasts thus produced and of the industrial production of ethanol from said yeasts. More especially, the present invention relates, in the most general aspect thereof, to a method for preparing yeasts from "industrial" *Saccharomyces cerevisiae* strains, to said yeasts and to the use thereof in the industrial production of ethanol from industrial media containing at least one pentose.

The common point of the approaches of the prior art of the field consists of methods aimed at improving "laboratory" strains with a known and/or constructed genetic inheritance and the abilities of which to produce ethanol are studied in general in media and under standardized and optimal laboratory conditions.

Indeed, the scientific literature and the patent documents analyzed by the applicant most commonly teach methods for obtaining haploid or diploid strains which are weakly tolerant to stresses, in particular for strong concentrations of ethanol and/or to high temperatures and/or to fermentation inhibitors. In addition, these methods mostly require having recourse, for these strains, to the use of auxotrophic markers and/or markers for resistance to antibiotics which can prevent them from being subsequently used in an industrial medium for obvious reasons of cost, or even sometimes for public health reasons.

The growth properties of these strains previously developed are generally insufficient, and these strains have never been confronted with industrial-scale biomass production imperatives, namely, to cite but three: high growth rate, ability to be dried, storage stability.

While "fermentative" performance levels (ability to produce ethanol anaerobically) are obtained in synthetic or defined "laboratory" media with these prior strains, they are not generally transposable to industrial media comprising complex mixtures resulting, for example, from residues for the treatment of cellulosic or lignocellulosic materials which contain toxic compounds that can inhibit the cell machinery of the yeast at various levels, in particular furfural, HMF, phenolic derivatives and acetic acid. In addition, the ability of these prior ethanol-producing processes to undergo scaling up is rarely documented.

The applicant has thus noted that there remains the need for a method for preparing an "industrial" yeast which takes into account both the constraints of the yeast manufacture and at the same time those of the final user in the applications thereof, in particular in terms of industrial production of ethanol at low cost and high yield.

The present invention aims precisely to meet this dual need.

Thus, the first subject of the present invention is a method for preparing an industrial *Saccharomyces cerevisiae* yeast strain capable of producing ethanol from a medium containing at least one pentose, and which comprises the following steps consisting in:
(i) selecting and obtaining an "industrial" *Saccharomyces cerevisiae* yeast strain capable of producing high concentrations of ethanol, of at least 14.5% (v/v), and preferably at least 16%, on a cereal hydrolysate, under simultaneous saccharification and fermentation (SSF) conditions and at a temperature of 35° C.,
(ii) Integrating at least one expression or deletion cassette into the genome of the yeast of step (i), said at least one cassette being chosen from the group consisting of:
 a. the association of the type open reading frame (ORF) of the *Pichia stipitis* XRm gene encoding the mutated xylose reductase enzyme which uses NADH;H+ as a preferential cofactor instead of NADPH;H+/*Saccharomyces cerevisiae* promoter and terminator, said cassette being flanked upstream and downstream by recombinogenic regions allowing its targeted integration into the genome,
 b. the association of the type open reading frame (ORF) of the *Pichia stipitis* XDH gene encoding the xylitol dehydrogenase enzyme/*Saccharomyces cerevisiae* promoter and terminator, said cassette being flanked upstream and downstream by recombinogenic regions allowing its targeted integration into the genome,
 c. the association of the type open reading frame (ORF) of the *Saccharomyces cerevisiae* XKS1 gene encoding the xylulokinase enzyme/*Saccharomyces cerevisiae* promoter and terminator, said cassette being flanked upstream and downstream by recombinogenic regions allowing its targeted integration into the genome,
(iii) inducing the expression of at least one gene of each step of the nonoxidative part of the pentose phosphate pathway by placing it under the control of a promoter of a glycolysis gene which is strongly expressed during alcoholic fermentation, and
(iv) deleting at least two copies of the open reading frame (ORF) of the *Saccharomyces cerevisiae* GRE3 gene encoding an aldose dehydrogenase.

The method according to the invention has, in particular, the following advantages:
for the yeast manufacturer, it makes it possible:
to construct a prototrophic, aneu/polyploid *Saccharomyces cerevisiae* yeast strain in order to allow the production of biomass on simple carbon, nitrogen and phosphorus sources in inexpensive media such as the byproducts of the sugar industry, for instance melasses,
to have a *Saccharomyces cerevisiae* yeast strain which exhibits a maximum growth rate ($\mu$ max) of between $0.37\ h^{-1}$ and $0.5\ h^{-1}$,
to have a *Saccharomyces cerevisiae* yeast strain which, when it is produced according to a method as described in the reference book "Yeast Technology" (2nd edition, 1991, G. Reed and T. W. Nagodawithana, published by Van Nostrand Reinhold, ISBN 0-442-31892-8), makes it possible to obtain a biomass production yield of at least 45 g of yeast dry matter per 100 g of sucrose equivalent processed,
to have a *Saccharomyces cerevisiae* yeast strain resistant to the drying process as described in patent documents EP 511108 and U.S. Pat. No. 5,741,695, wherein the loss of fermentative activity after drying must not exceed 30%,
to produce, under industrial conditions (in particular inexpensive medium, good biomass yield, ready-to-use dry yeast), a fresh or dry yeast from a *Saccharomyces cerevisiae* yeast strain which is genetically stable, which is robust since it is particularly tolerant to high concentrations of ethanol and which is capable of producing, from for example hemicellulosic biomass, ethanol at at least 80 g/L, this being at a high temperature of about from 30 to 40° C.

Moreover, for the ethanol producer, the advantage of the method according to the invention is to have an active yeast (fresh—liquid or compressed—or dried), obtained according to a method of production as described in the handbook "Yeast Technology", from a *Saccharomyces cerevisiae* yeast strain as defined in the preceding paragraph which is:

capable, under the SSF conditions described in patent document WO 2004/046333, of fermenting, at 35° C., a cereal hydrolysate up to an ethanol concentration of at least 14.5% (v/v), capable, under the SSF conditions described in patent document WO 2004/046333, of fermenting, at 35° C., a cereal hydrolysate up to an ethanol concentration of at least 16% (v/v).

The results of the method according to the invention are all the more notable since they were obtained from a prototrophic, aneu/polyploid "industrial" strain which, as a result, has a genetic material which is much more complex than that of a "laboratory" strain, making the consequences of modifications of said industrial strain unforeseeable to say the least. This complex genetic background, specific to industrial strains, makes it all the more difficult to obtain genetically modified strains which are free in the end of antibiotic resistance markers, in particular when numerous genetic targets are to be modified. Strains free of antibiotic resistance markers are quite obviously preferable for health and environmental reasons.

The applicant has shown that the genetic modifications according to the method of the invention, applied to an industrial strain with a complex genetic inheritance and which has a capacity for producing high concentrations of ethanol do not induce any genomic instability.

The prototrophic strains according to the invention have the advantage of growing on simple carbon, nitrogen and phosphorus sources.

However, this characteristic means that the transformation vectors available in the scientific community (vectors using auxotrophic markers) are ineffective.

It is therefore necessary to have available tools/vectors which use antibiotic resistance markers, these said tools/vectors being advantageously constructed so as to ultimately allow the excision of these markers. The construction of the yeasts in accordance with the invention has required, for example, the use of 4 different positive markers (geneticin, phleomycin, hygromycin and blasticidin).

The strains in accordance with the invention are aneu/polyploids: this is a feature generally encountered in industrial yeasts which are derived from the natural environment. The phylogenetic past of these strains is responsible for this particularity.

However, it is an additional difficulty encountered when wishing to disrupt/inactivate all the copies of a given gene. However, this aneu-polyploid characteristic is generally responsible for many properties of interest of industrial yeasts (growth rate, resistance to various stresses, phenotypic stability).

In addition, the present inventors, after lengthy research, have noted with surprise that, with the method according to the invention, implemented using the "industrial" strain that they had selected:

the introduction of expression and deletion cassettes does not induce any genomic instability in the modified yeast, which experiences an improvement in its genetic inheritance, it is not obligatory to regulate its XK activity. There is in fact a controversy in the prior art regarding the overexpression of XKS1 in laboratory strains, which are therefore better defined, which suggests that the xylulokinase activity should be finely regulated (Jin et al AEM 2003, 69,495-503 vs Ho et al. 1999, Advances in Biochemical Engineering/Biotechnology, Vol. 65, pp. 163-192).

In particular, the inventors have shown that, with said industrial strain, it is possible to carry out:

the deletion of at least two copies of the *S. cerevisiae* GRE3 gene (the Gre3p enzyme being an aldose reductase which consumes NADPH;H+ which is produced to a larger extent via the oxidative part of the pentose pathway) in said industrial strain according to the invention, making it possible to reduce accordingly the consumption of NADPH;H+ by said enzyme, the overexpression of XKS1 naturally, that is to say that step c) of the method according to the invention can be omitted, given that XKS1 is an endogenous *S. cerevisiae* gene. This overexpression can in particular be made possible after cyclic cultures when the method comprises a subsequent directed evolution step, as described below.

As a preferred variant of this first subject, the cassettes a), b) and c) of step (ii) are all integrated.

For its constructs, the applicant first of all examined the effect of the wild-type XR gene of *Pichia stipitis*. After removal of the markers and a directed evolution step, it obtained the strains EG4 and EG5 deposited with the CNCM [French National Collection of Microorganism Cultures] under Nos. CNCM I-4397 and I-4398, on Nov. 23, 2010.

However, even though the EG4 and EG5 strains obtained are faster than the EG1 and EG2 strains, they produce on average 50% more xylitol. The xylitol leads to a diversion of the carbon and significantly reduces the ethanol-to-sugar conversion yield, which is very prejudicial given the industrial application intended.

The applicant subsequently replaced the wild-type XR gene of *Pichia stipitis* with a mutated gene XRm, and noted that it is preferable for the XRm gene to be a gene which has the following mutation, K270M, or a mutated XR gene which has one (of the) different mutation(s) such as K270R described by Watanabe et al., Microbiol. 2007, 153, 3044-3054, such that this mutation confers on the encoded enzyme the use of NADH;H+ as a preferential cofactor in place of NADPH;H+.

The difference between these two xylose reductases is that one carries a methionine in position 270 (K270M) in place of a lysine residue, while the other carries an arginin (K270R) in place of a lysine residue.

The applicant has noted that the K270R modification reduces the affinity of XR for NADPH;H+ and increases its ability to use NADH;H+. Furthermore, this modification induces a decrease in the diversion of xylose to xylitol and makes it possible to improve the xylose-to-ethanol conversion yield under fermentation conditions.

Even more preferably, in this variant, the cloning of the mutated XR gene (XRm) is carried out by single-copy clone.

It is also preferable in this variant for said at least one gene of each step of the nonoxidative part of the pentose phosphate pathway of step (iii) to be chosen from the group consisting of RPE1, RKI1, TKL1 and TAL1, and for said promoter of a glycolysis gene which is strongly expressed during alcoholic fermentation to be chosen from the group consisting of the TDH3 promoter for RPE1, RKI1 and TKL1 and the PGK1 promoter for TAL1.

According to supplementary or alternative characteristics, in the method for preparing an industrial *Saccharomyces cerevisiae* yeast strain in accordance with the invention:
the promoter in step (ii) is chosen from the group consisting of ADH1, ADH2, PGK1, TDH3, PDC2 and GAL1/10, preferably ADH1, and the terminator consists of CYC1 or of the modified gene's own terminator, for instance the TAL1 terminator for the TAL1 gene;
a subsequent directed evolution step is provided for, which comprises the following successive steps consisting in subjecting the yeast obtained to
(i) a mutagenesis,
(ii) growth in cyclic cultures under limited $O_2$ in a medium containing said at least one pentose, and
(iii) a selection by aerobic growth on a solid medium containing glycerol as sole carbon source,
so as to obtain non-respiratory-deficient mutants of said yeast which exhibit an aerobic growth in the presence of a medium containing said at least one pentose.

Preferably in this variant, the mutagenesis of step (i) is carried out under moderate conditions, mainly moderate mutagenesis with 100 to 500 $J/cm^2$, and more preferably 300 $J/cm^2$ of ultraviolet radiation at 254 nm. These conditions cause only a mortality of 10% of the population subjected to the ultraviolet radiation.

The inventors have thus shown, surprisingly, that with such a low controlled mortality, it is possible to reduce by a factor of 10 the duration of the step of directed evolution via cyclic cultures which is necessary for obtaining mutants capable of fermenting said at least one pentose. The survival rate is determined by taking out, on agar dishes containing a nutritive medium, an identical volume of the cell suspension before and after mutagenesis. The number of colonies is determined after 48 h of growth.

Preferably, the $O_2$ limitation in step (ii) of this variant is carried out by virtue of a partial overpressure in the equipment used (for example, flasks or fermenters) due to the $CO_2$ produced.

The cyclic cultures according to this variant, under the conditions of fermentation of said at least one pentose, make it possible to enrich the population in mutants capable of fermenting said pentose, in a time of from 4 to 8 weeks and preferably 6 weeks, which is relatively short and very advantageous compared with what would be obtained by chemostat as described by Kuyper et al. (2004) 4, 655-664.

Although the "small" respiratory-deficient phenotype may be in accordance with the criteria for fermentation of said at least one pentose, in this variant, the present inventors have carried out a step of removing the "small" yeasts since this phenotype is incompatible with the methods for producing industrial yeasts within the meaning of the invention.

The subject of the present invention is also the industrial *Saccharomyces cerevisiae* yeast strain EG3 directly obtained by the method according to the invention before the directed evolution step and which consists of the yeast strain deposited on Apr. 14, 2010, with the CNCM (National Collection of Microorganism Cultures of the Institut Pasteur) under No. I-4295 under the conditions of the treaty of Budapest.

The subject of the present invention is also the industrial *Saccharomyces cerevisiae* yeast strain EG2 directly obtained by means of the method according to the invention after the directed evolution step and which consists of the yeast strain deposited on Apr. 14, 2010, with the CNCM (National Collection of Microorganism Cultures of the Institut Pasteur) under No. I-4294 under the conditions of the treaty of Budapest.

The subject of the present invention is also the industrial *Saccharomyces cerevisiae* yeast strain EG1 directly obtained by means of the method according to the invention after the directed evolution step and which consists of a variant, which is incapable of sporulating, of the EG2 yeast strain, which was deposited on Apr. 14, 2010, with the CNCM (National Collection of Microorganism Cultures of the Institut Pasteur) under No. I-4293 under the conditions of the treaty of Budapest.

A strain incapable of sporulating has an advantage in terms of protection of the environment since it eliminates the risk of dissemination of the transgenes by conjugation with other yeasts in the surrounding environment. This characteristic is all the more important when the genetically modified microorganisms are used on a very large scale.

The subject of the present invention is also the industrial *Saccharomyces cerevisiae* yeast strain EG9 directly obtained by means of the method according to the invention after the directed evolution step and which consists of the yeast strain deposited on Mar. 1, 2011, with the CNCM (National Collection of Microorganism Cultures of the Institut Pasteur) under No. I-4450 under the conditions of the treaty of Budapest.

More preferably,
the industrial *Saccharomyces cerevisiae* yeast strain obtained is practically or totally free of markers, in particular antibiotic resistance markers.

The *Saccharomyces cerevisiae* yeast strains prepared in accordance with the present invention, according to the criteria defined above, retained, after introduction of the genetic modifications and other mutations generated during the directed evolution step, their genotypic and phenotypic characteristics after a complete industrial production process. In particular, the yeasts produced exhibit alcohol production kinetics, xylose consumption kinetics and a maximum amount of alcohol produced which are rigorously identical to the yeast strain before the application of a complete industrial process.

Moreover, the industrial characteristics of the strain chosen before manipulation, as previously described (growth rate, production yield, ability to be dried) remain unchanged.

The subject of the present invention is also a method for producing ethanol, from a medium containing at least one pentose, by fermentation using a yeast according to the invention, mentioned above, or as obtained by means of a method in accordance with the invention, as has just been described.

Preferably, the method for producing ethanol has the following alternative and/or supplementary characteristics:
it comprises a step of simultaneous saccharification and fermentation (SSF) in the presence of polymers of hexoses, predominantly consisting of glucose, and of at least one enzyme capable of hydrolyzing them,
said at least one pentose is xylose,
said medium is chosen from the group consisting of lignin hydrolysates, cellulose hydrolysates, hemicellulose hydrolysates, and dextrin hydrolysates,
the average rates of release of the hexoses, predominantly of the glucose, are about from 2.8 to 5.6 g/L/h with a zero extracellular concentration of hexose, predominantly of glucose.

The present inventors implemented the method for producing ethanol in accordance with the invention under the real SSF (simultaneous saccharification and fermentation) conditions, as carried out in the industry for ethanol production, in particular in the USA.

The sugar concentrations used (70 g/kg of xylose and 130 g/kg of glucose equivalent) are, to the applicant's knowledge, the maximum concentrations that can be encountered in practice. All the published tests referring to fermentation of xylose were carried out with much lower total sugar concentrations.

Figure 2:
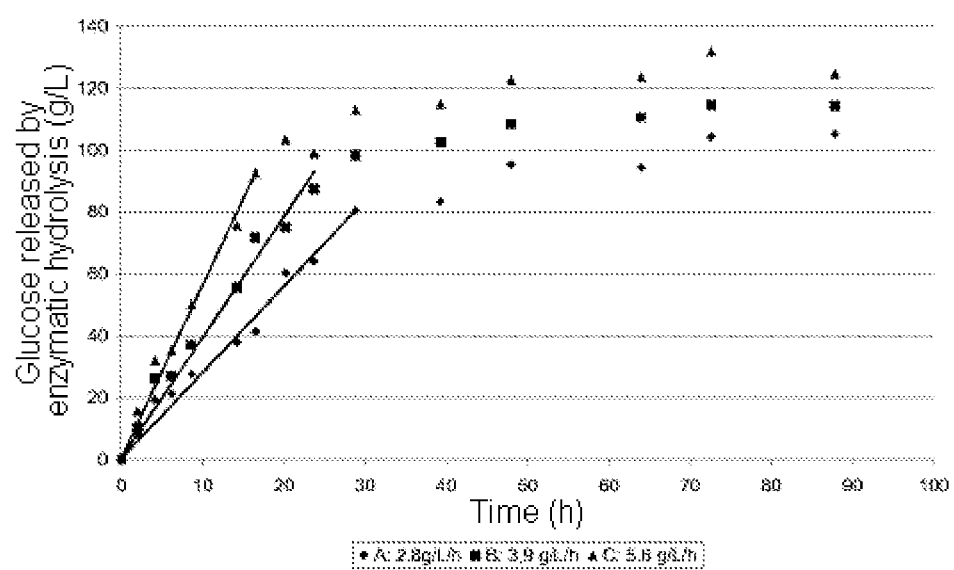
Figure 3:
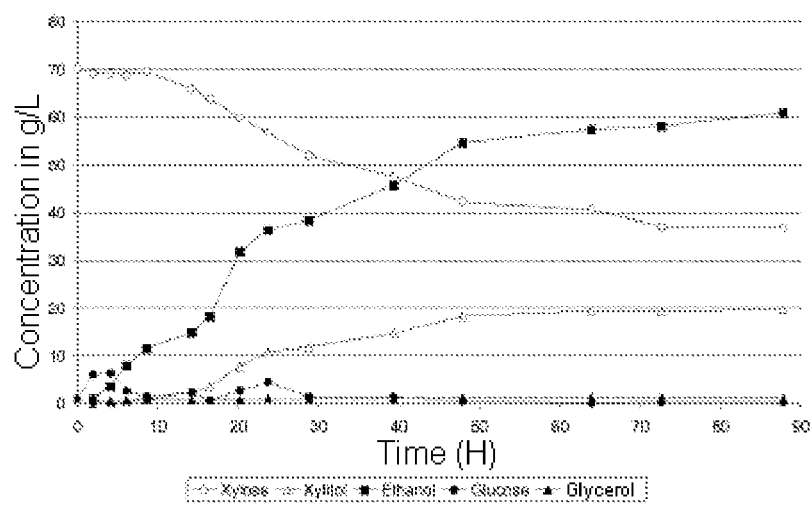
Figure 4:
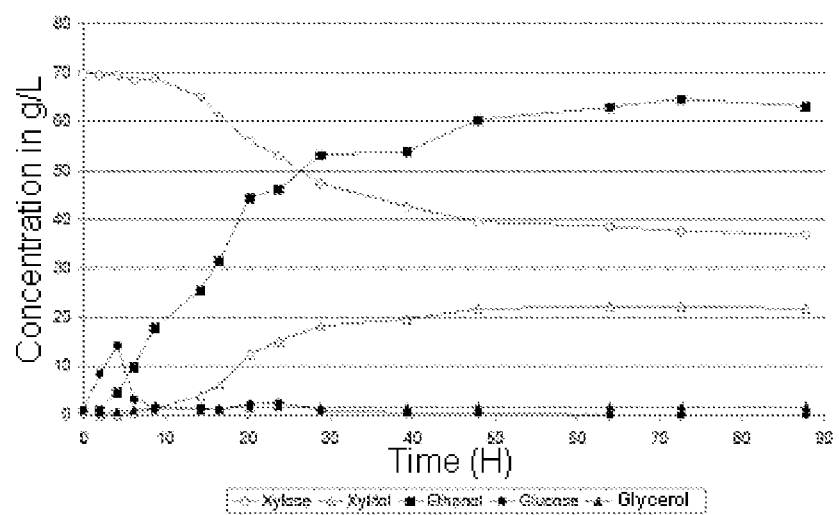
Figure 5:
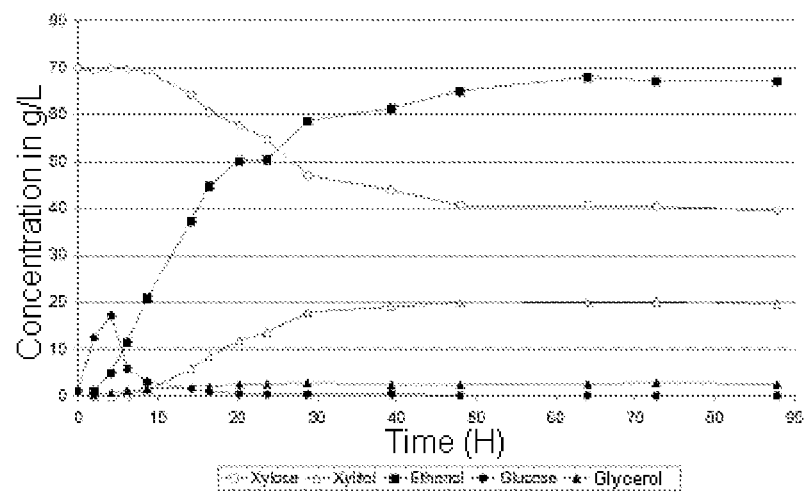
Figure 6:
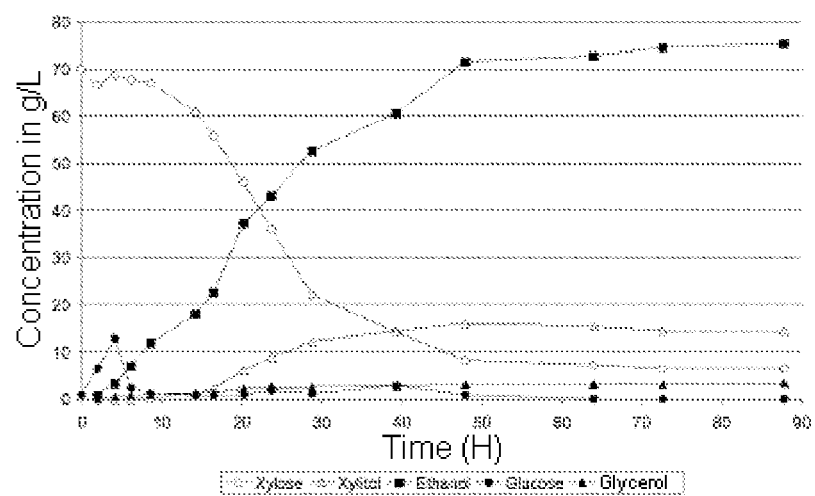
Figure 7:
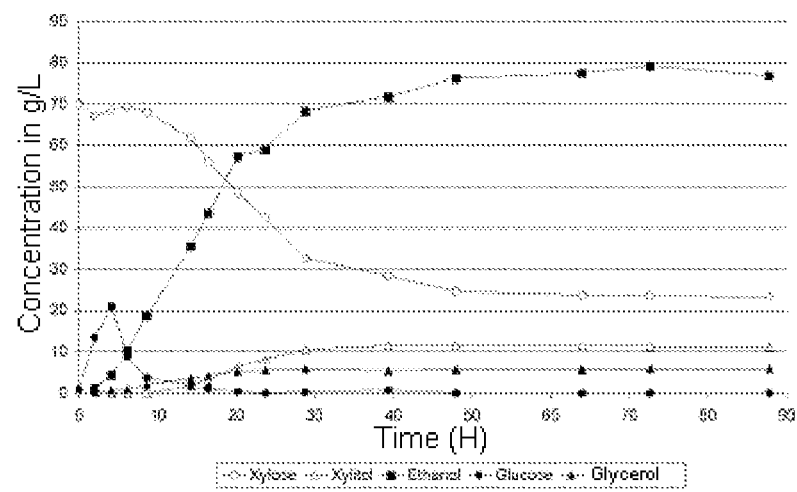
Figure 8:
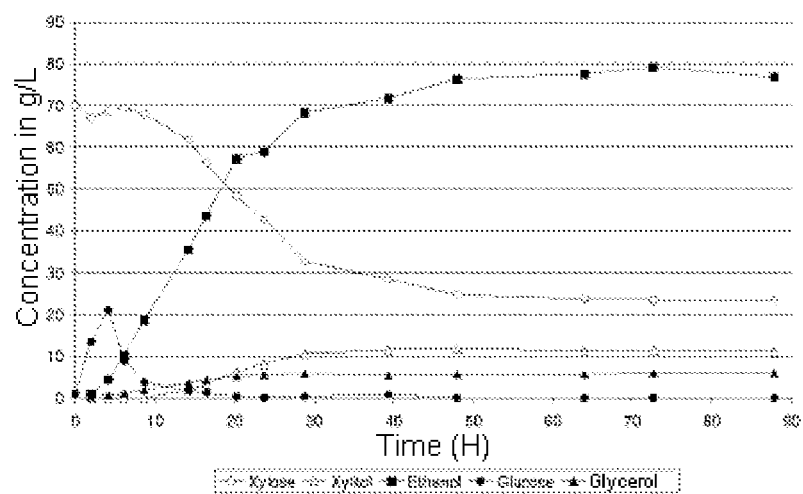
Figure 9:
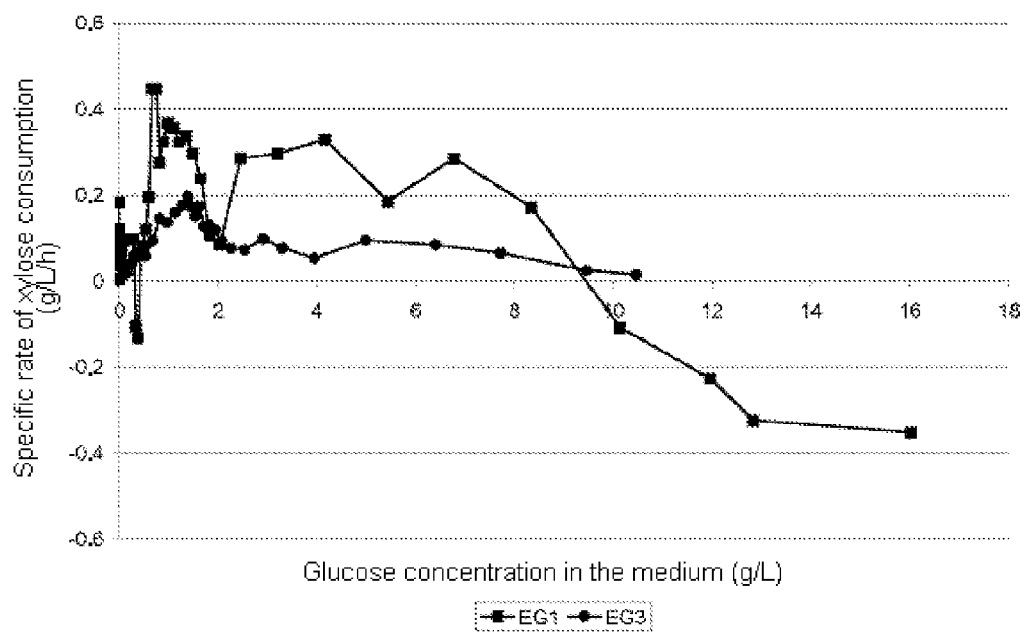
Figure 10:
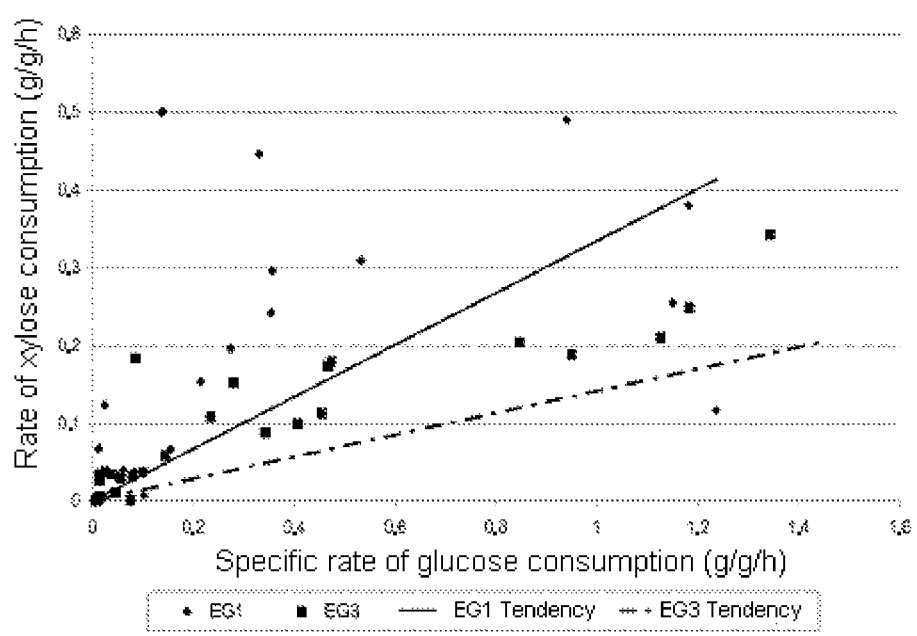
Figure 11:
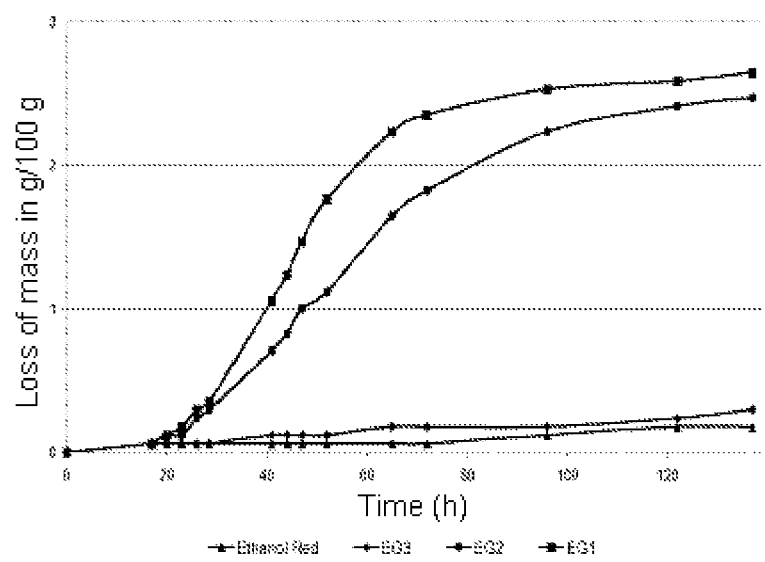
Figure 12:
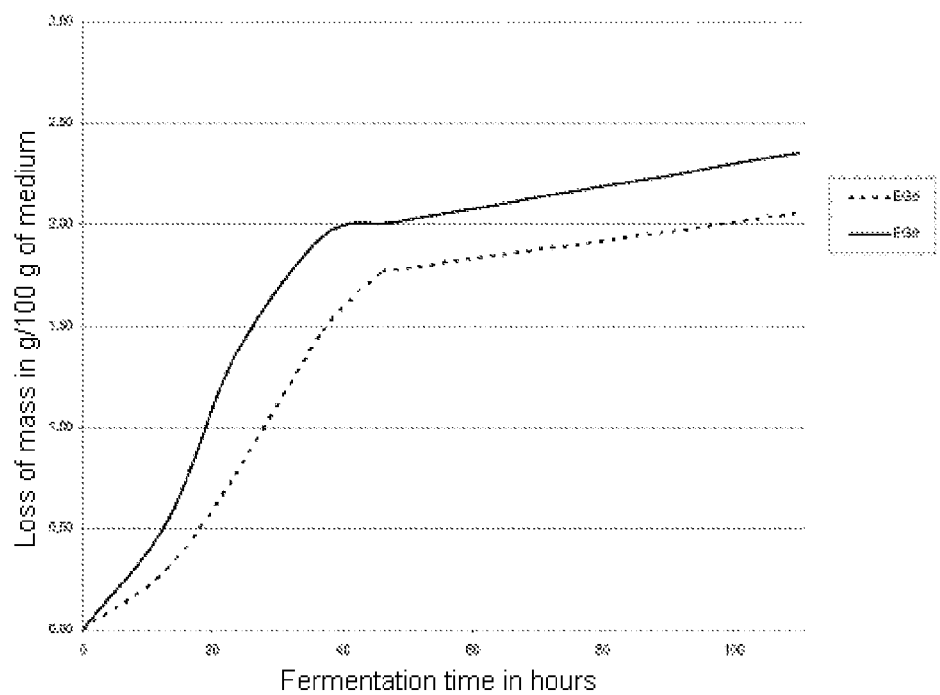

Other characteristics and advantages of the invention will emerge even more clearly on reading the detailed description which follows, comprising exemplary embodiments with results tables which are given purely by way of nonlimiting illustration, and for the understanding of which reference will be made to the appended drawings in which:

FIG. 1 illustrates a vector for overexpression of *Pichia stipitis* XDH,

FIG. 2 is a graph showing the glucose released by enzymatic hydrolysis as a function of time according to three initial release conditions (A): 2.8 g/L/h, (B): 3.9 g/L/h and (C): 5.6 g/L/h, FIGS. 3 to 5 show, for a strain in accordance with the invention EG3, the change in the glucose, xylose, ethanol, xylitol and glycerol concentrations over time; FIG. 3 corresponds to the dose of enzyme A, FIG. 4 to the dose of enzyme B and FIG. 5 to the dose of enzyme C, FIGS. 6 to 8 show, for yet another strain in accordance with the invention EG1, the change in the glucose, xylose, ethanol, xylitol and glycerol concentrations over time; FIG. 6 corresponds to the dose of enzyme A, FIG. 7 to the dose of enzyme B and FIG. 8 to the dose of enzyme C, FIG. 9 shows the change in the moving averages of the rates of consumption of xylose by each of the two strains EG1 and EG3 over the course of the three tests carried out, as a function of the moving average of the glucose concentrations in the medium over the same time period, FIG. 10 is a graph illustrating the specific rate of production of xylitol (g/L/h) as a function of the specific rate of consumption of xylose in the medium (g/L/h) for the two strains EG1 and EG3, FIG. 11 is a graph illustrating the loss of mass as a function of fermentation time in the presence of xylose (70 g/L) by the 2 evoluates EG3 and EG2 (the Ethanol Red™ strain is the starting strain), FIG. 12 illustrates the change in the loss of mass observed during the fermentation of xylose by the EG5 and EG9 strains. The cells were inoculated in an amount of 1 g/kg of dry matter into a medium containing 70 g/kg of xylose. The fermentation was carried out at 32° C.

EXAMPLES

Example 1

The selection of the industrial strain is as described in the description above.

All the DNA sequences which were used for the various transformations targeting the overexpression of a gene were obtained from a known standard vector (*E. coli* pUC type) in which the following were available:
 the integration targets;
 the promoters/terminators chosen per a gene of interest, and
 the resistance markers that will be subsequently eliminated (see below).

An example of a vector used for the overexpression of *Pichia stipitis* XDH is illustrated in FIG. 1.

For the disruption of the copies of the GRE3 gene of the industrial strain selected, the inventors used material PCR-amplified from a plasmid of pUG6 type (Güldener U, Heck S, Fielder T, Beinhauer J, Hegemann J H. Nucleic Acids Res. 1996 Jul. 1; 24(13):2519-2524).

The yeast transformation step was carried out according to Gietz, R. D. and R. A. Woods. (2002) Transformation of yeast by the Liac/SS Carrier DNA/PEG method. Methods in Enzymology 350: 87-96.

The yeast strains according to the invention, respectively EG1, EG2 and EG3, were deposited with the CNCM on Apr. 14, 2010, and the numbers I-4293, I-4294 and I-4295, respectively, were assigned thereto.

The strains in accordance with the invention have, according to one preferential mode, the following genotype:
 Ethanol Red™, BUD5::ADH1p-PsXRm (K270M)-CYC1t; HO::ADH1p-PsXDH-CYC1t; BUD5::ADH1p-XKS1-CYC1t; RPE1::TDH3p-RPE1-CYC1t; RKI1::TDH3p-RKI1-CYC1t; TKL1::TDH3p-TKL1-CYC1t; TAL1::PGK1p-TAL1-CYC1t; ΔGRE3

Example 2

The mutagenesis of the strains obtained in the previous example was carried out moderately, namely from 100 to 500 J/cm$^2$ and preferably at 300 J/cm$^2$ of ultraviolet radiation at 254 nm.

After one week of culture at 32° C. in a medium of YE type (Yeast Extract 0.5%) containing 7% of xylose, with stirring, without aeration—the $O_2$ limitation being realized by virtue of a partial overpressure in the flasks due to the $CO_2$ produced during the fermentation—one ml of the culture is used to re-inoculate the same medium. This operation is repeated 6 times. The cells are finally plated out on YE agar medium containing glucose at 20 g/L. Isolated colonies are removed and then cultured successively on:
 YE Glycerol at 20 g/L and under aerobic conditions in order to eliminate the "small" mutants, i.e. respiratory-deficient mutants;
 YE Glucose in order to verify their growth rate;
 YE xylose in order to identify the most advantageous clones.

Example 3

The inventor first of all tested, in anaerobic batch culture, the strains genetically modified so as to be capable of converting xylose to ethanol, as obtained in example 2.

They were able to measure the apparent Km for the xylose by measuring the rate of production of $CO_2$ as a function of the xylose concentration, during the fermentation of the xylose as sole carbon source: it is 6.16 M.

Among the strains tested, three are selected under SSF conditions in order to evaluate their capacity for metabolizing xylose at the same time as glucose. The SSF tests were carried out with low doses of enzymes, the activity of which is between 4.3 and 8.6 µKat, in order for the glucose release rate to be low and for the concentration of residual glucose during the fermentation to be zero.

The strains tested were the EG3 strain and the EG1 strain, respectively obtained before and after the directed evolution step. The cells of the EG1 strain are incapable of sporulating. The ability of these cells to sporulate is determined by microscopic observation of tetrads or asci obtained by culturing the cells for 48 h on a poor medium of SAA type (0.8% sodium acetate, 1.5% agar).

Test Conditions

The tests were carried out at 32° C., pH 5. The inoculation was 0.5 g of yeast dry matter per kg of initial must. The gradual enzymatic release of the glucose was obtained through the use of dextrins and the addition of glucoamylase. The glucoamylase doses used were low (between 4.3 µkat and 8.6 µkat) in order to simulate kinetics of hydrolysis of the cellulose by cellulases taking place in 72 h. The rates of initial glucose release that were tested were, respectively, (A): 2.8 g/L/h, (B): 3.9 g/L/h and (C): 5.6 g/L/h.

As generally observed, the hydrolysis kinetics decrease when 60-70% of the dextrins have been hydrolyzed and the average rates of glucose release are subsequently about 0.4-0.45 g/L/h for the three conditions with a slightly faster rate with condition A (FIG. 2).

In practice, the medium used is a synthetic medium containing yeast extract (5 g/kg), urea (2.5 g/kg), dipotassium phosphate (1 g/kg), a 12 mM citrate buffer and also minerals and vitamins.

Results Obtained

EG3 Strain

FIGS. 3 to 5 give the change in the glucose, xylose, ethanol, xylitol and glycerol concentrations over time. These figures show that, in 72 h:
- the EG3 strain consumed between 30 and 33 g of xylose according to the tests, whereas it had consumed virtually none in xylose batch mode;
- 17 to 20 g of xylitol were produced out of the 30-33 g of xylose consumed, i.e. a ratio of 0.5 g/g for condition A and a ratio of 0.6 g/g for conditions B and C;
- the amounts of glycerol produced were low, lower than the amounts expected in this type of test.

Overall, the three tests gave equivalent results.

TABLE 1

Molecules produced and consumed by the EG3 strain (in g per kg of initial medium at 72 h)

| Enzyme dose | Glucose | Xylose | Bio-mass | Xylitol | Glyc-erol | Ethanol | Carbon balance |
|---|---|---|---|---|---|---|---|
| A | 103.3 | 32.8 | 10 | 17.0 | 1.1 | 51.7 | 101% |
| B | 114.4 | 33.2 | 10 | 19.6 | 1.6 | 57.7 | 103% |
| C | 122.2 | 30.9 | 10 | 17.9 | 2.5 | 60.6 | 103% |

EG1 Strain

FIGS. 4 to 6 give the change in glucose, xylose, ethanol, xylitol, and glycerol concentrations over time. These figures show that, in 72 h:
- the EG1 strain consumed between 45 and 60 g of xylose according to the tests, i.e. virtually twice as much as the EG3 strain;
- 10 to 13 g of xylitol were produced out of the 45-60 g of xylose consumed, i.e. a ratio of 0.2 g/g for the three tests;
- the amounts of glycerol produced were low, but higher than with the EG3 strain.

Overall, the tests gave equivalent results.

TABLE 2

Molecules produced and consumed by the EG1 strain (in g per kg of initial medium at 72 h)

| Enzyme dose | Glucose | Xylose | Bio-mass | Xylitol | Glyc-erol | Ethanol | Carbon balance |
|---|---|---|---|---|---|---|---|
| A | 102.5 | 60.61 | 10 | 12.74 | 2.86 | 65.49 | 100% |
| B | 115.6 | 51.65 | 10 | 11.90 | 4.17 | 69.34 | 102% |
| C | 120.9 | 45.96 | 10 | 9.86 | 5.33 | 70.18 | 103% |

Observations/hypotheses regarding the results obtained, in particular relating to the glucose concentration allowing taking of the xylose.

The results obtained on glucose-xylose batch show a break in the slope of loss of mass which appears to indicate that the glucose was first consumed and then the xylose was subsequently consumed at a much lower rate.

The SSF test as carried out in the example makes it possible to evaluate whether the taking of the xylose would be greater with non-zero incoming glucose flow but zero glucose concentration.

FIG. 9 shows the change in the moving averages of the rates of xylose consumption by each of the two strains over the course of the three tests carried out, as a function of the moving average of the glucose concentrations in the medium over the same time period.

The results make it possible to note:
- that there is xylose consumption by the strains tested at around 5 g/kg of glucose in solution,
- that the xylose consumption rate observed with the EG3 strain is half those observed with the EG1 strain.

In a preferred variant of the method for producing ethanol according to the invention, as presented in the example, the slow and controlled release of the glucose allows the cells not to undergo a strong variation of osmotic pressure and to avoid the clogging of the fermentative pathways (glycolysis, pentose phosphates, and sugar transporters) that would limit the use of the xylose.

Surprisingly and notably, with the method according to the invention, the cells are capable of metabolizing 62 g/L of xylose in 50 hours in a medium very rich in carbon sources of about 200 g/L (example carried out with 130 g/L of glucose equivalent and 70 g/L of xylose). Such drastic conditions as these have never, to our knowledge, been described.

According to the SSF tests carried out:
- the specific rate of the EG1 strain is 0.5 g xylose/g DM yeast/h;
- 12.74 g of xylitol were formed for 60.61 g of xylose consumed, i.e. a ratio of 21 g/100 g.

The invention claimed is:

1. A *Saccharomyces cerevisiae* yeast strain selected from the group consisting of the *Saccharomyces cerevisiae* yeast strain EG3 deposited on Apr. 14, 2010 at the CNCM (National Collection of Microorganism Cultures of the Institut Pasteur) under No. I-4295, the *Saccharomyces cerevisiae* yeast strain EG2 deposited on Apr. 14, 2010 at the CNCM under No. I-4294, the *Saccharomyces cerevisiae* yeast strain EG1 deposited on Apr. 14, 2010 at the CNCM under No. I-4293, and the *Saccharomyces cerevisiae* yeast strain EG9 deposited on Mar. 1, 2011 at the CNCM under No. I-4450.

2. The *Saccharomyces cerevisiae* yeast strain according to claim 1 which is the *Saccharomyces cerevisiae* yeast strain EG2 deposited on Apr. 14, 2010 at the CNCM (National Collection of Microorganism Cultures of the Institut Pasteur) under No. I-4294.

3. The *Saccharomyces cerevisiae* yeast strain according to claim 1 which is the *Saccharomyces cerevisiae* yeast strain EG1 deposited on Apr. 14, 2010 at the CNCM (National Collection of Microorganism Cultures of the Institut Pasteur) under No. I-4293.

4. The *Saccharomyces cerevisiae* yeast strain according to claim 1 which is the *Saccharomyces cerevisiae* yeast strain EG9 deposited on Mar. 1, 2011 at the CNCM (National Collection of Microorganism Cultures of the Institut Pasteur) under No. I-4450.

5. A method for producing ethanol from a medium containing at least one pentose comprising a step of fermenting a yeast as claimed in claim 1.

6. The method as claimed in claim 5, further comprising a step of simultaneous saccharification and fermentation (SSF) in the presence of polymers of hexoses and of at least one enzyme capable of hydrolysing them.

7. The method as claimed in claim 5, wherein said at least one pentose is xylose.

8. The method as claimed in claim 5, wherein said medium is chosen from the group consisting of lignin hydrolysates, cellulose hydrolysates, hemicellulose hydrolysates and dextrin hydrolysates.

9. The method as claimed in claim 6, wherein the average rates of release of the hexoses are about from 2.8 to 5.6 g/L/h with a zero extracellular concentration of hexose, predominantly of glucose.

10. The method as claimed in claim 6, wherein the polymers of hexoses predominantly consist of glucose.

11. The *Saccharomyces cerevisiae* yeast strain according to claim 1 which is the *Saccharomyces cerevisiae* yeast strain EG3 deposited on Apr. 14, 2010 at the CNCM (National Collection of Microorganism Cultures of the Institut Pasteur) under No. I-4295.

* * * * *